US011643680B2

(12) United States Patent
Liu

(10) Patent No.: US 11,643,680 B2
(45) Date of Patent: *May 9, 2023

(54) DIRECT QUANTIFICATION OF UNPROCESSED NUCLEIC ACID SAMPLES

(71) Applicant: LIFE TECHNOLOGIES CORPORATION, Carlsbad, CA (US)

(72) Inventor: Jason Yingjie Liu, Foster City, CA (US)

(*) Notice: Subject to any disclaimer, the term of this patent is extended or adjusted under 35 U.S.C. 154(b) by 106 days.

This patent is subject to a terminal disclaimer.

(21) Appl. No.: 17/209,957

(22) Filed: Mar. 23, 2021

(65) Prior Publication Data

US 2021/0285037 A1  Sep. 16, 2021

Related U.S. Application Data

(60) Division of application No. 16/403,012, filed on May 3, 2019, now Pat. No. 10,968,476, which is a continuation of application No. 15/029,088, filed as application No. PCT/US2014/055602 on Sep. 15, 2014, now abandoned, which is a continuation of application No. 14/056,921, filed on Oct. 17, 2013, now abandoned.

(51) Int. Cl.
  *C12P 19/34* (2006.01)
  *C12Q 1/6851* (2018.01)
  *C12Q 1/6806* (2018.01)
  *C12Q 1/686* (2018.01)

(52) U.S. Cl.
  CPC .......... *C12Q 1/6851* (2013.01); *C12Q 1/686* (2013.01); *C12Q 1/6806* (2013.01)

(58) Field of Classification Search
  CPC ..... C12Q 1/6851; C12Q 1/686; C12Q 1/6806
  See application file for complete search history.

(56) References Cited

U.S. PATENT DOCUMENTS

| 6,645,717 B1 | 11/2003 | Smith et al. |
| 9,708,644 B2 | 7/2017 | Liu et al. |
| 2003/0113906 A1 | 6/2003 | Sangha et al. |
| 2006/0008903 A1 | 1/2006 | Mussivand |
| 2009/0098559 A1 | 4/2009 | Caragine et al. |
| 2011/0008785 A1 | 1/2011 | Tan et al. |
| 2013/0295572 A1 | 11/2013 | Liu et al. |
| 2015/0031031 A1 | 1/2015 | Harrold et al. |

FOREIGN PATENT DOCUMENTS

| WO | 2013/126765 A2 | 8/2013 |
| WO | 2014/072354 A1 | 5/2014 |
| WO | 2014/143714 A2 | 9/2014 |

OTHER PUBLICATIONS

"AmpFISTR Identifiler PCR Amplification Kit", Aug. 1, 2012 (Aug. 1, 2012).

Applied Biosystems, "Applied Biosystems 7500 Fast and 7500 Real-Time PCR Systems—Specification Sheet", Jan. 1, 2009, pp. 1-4.
Applied Biosystems. Quantifiler® Duo DNA Quantification Kit. User's Manual 2012.
Barbisin et al. Quantifiler (Registered) Duo DNA Quantification Kit: A Guiding Tool for Short Tandem Repeat Genotyping of Forensic Samples. J Forensic Res 2011 ;2(2):1-11.
Carla R. Santos et al: "Use of FTA elute card impregnated with cervicovaginal sample directly into the amplification reaction increases the detection of human papillomavirus DNA", At Brazilian Journal of Microbiology, vol. 43, No. 1, Jan. 1, 2012 (Jan. 1, 2012), pp. 389-392.
French, D. et al., "Interrogation of short tandem repeats using fluorescent probes and melting curve analysis: A step towards rapid DNA identity screening", Forensic Science International: Genetics, vol. 2, Issue 4, Sep. 2008, 333-339.
Gale, N. et al., "Rapid typing of STRs in the human genome by HyBeacon melting", Organic & Biomolecular Chemistry Issued 24, The Raval Society of Chemistry, 2008, 4553-4559.
International Preliminary Report on Patentability received for PCT Patent Application No. PCT/US2014/055602, dated Apr. 28, 2016, 10 pages.
Life Technologies Corporation, "AmpFISTR Identifiler PCR Amplification Kit", Life User Guide, 2012, pp. 1-142.
Liu, J. "Direct qPCR quantification using the Quantifiler Trio DNA quantification kit", Forensic Science International Genetics, vol. 13, 2014, pp. 10-19.
Liu, J. Y. et al., "Direct qPCR quantification of unprocessed forensic casework samples", Forensic Science International: Genetics, vol. 11, 2014, pp. 96-104.
Liu, Jason Yingjie: "Direct qPCR quantification of unprocessed forensic casework samples", Forensic Science International: Genetics, vol. 11, Jul. 5, 2014 (Jul. 5, 2014), pp. 96-104.
Liu, Jason Yingjie: "Direct qPCR quantification using the Quantifiler Trio DNA quantification kit", Forensic Science International: Genetics, vol. 13, Mar. 15, 2014 (Mar. 15, 2014), pp. 10-19.
Nozawa, N. et al. "Real-Time PCR Assay Using Specimens on Filter Disks as a Template for Detection of Cytomegalovirus in Urine", Journal of Clinical Microbiology, vol. 45, No. 4, 2007, pp. 1305-1307.
Nozawa, N. et al., "Real-Time PCR Assay Using Specimens on Filter Disks as a Template for Detection of Cytomegalovirus in Urine", Journal of Clinical Microbiology, vol. 45, No. 4, Apr. 2007, 1305-1307.

(Continued)

*Primary Examiner* — Kenneth R Horlick
(74) *Attorney, Agent, or Firm* — Workman Nydegger; Logan Christenson; John Guynn

(57) ABSTRACT

A workflow for direct qPCR quantification of unprocessed forensic casework samples is disclosed herein. 13 pg of DNA has been detected by direct amplification from a paper substrate. Direct qPCR quantification of unprocessed forensic casework samples and direct STR amplification of unprocessed forensic casework samples collected on the same PE-swab will greatly increase forensic laboratory's efficiency and capability.

20 Claims, 11 Drawing Sheets

(56) References Cited

OTHER PUBLICATIONS

Pak Yang Chum et al: "Direct PCR from blood preserved on Whatman FTA and 903 Cards using Phusion Blood Direct PCR Kit", Dec. 1, 2008 (Dec. 1, 2008), pp. 1-1.
PCT/US2014/055602 International Search Report and Written Opinion dated Dec. 2, 2014, 16 Pages.
Quinones, I. et al., "Cell free DNA as a component of forensic evidence recovered from touched surfaces", Forensic Science International: Genetics, vol. 6, Issue 1, Jan. 2012, 26-30.
Smith et al. Collecting, archiving and processing DNA from wildlife samples using FTA (Registered) databasing paper. BMC Ecology 2004:4:1-11.
Taylor et al. "Real-time PCR detection of Plasmodium directly from whole blood and filter paper samples", Malaria Journal, vol. 10, No. 244, 2011, pp. 1-8.
Wang et al. Direct amplification of STRs from blood or buccal cell samples. Forensic Sci Int: Genetics Supplement Series 2:113-4. (2009).

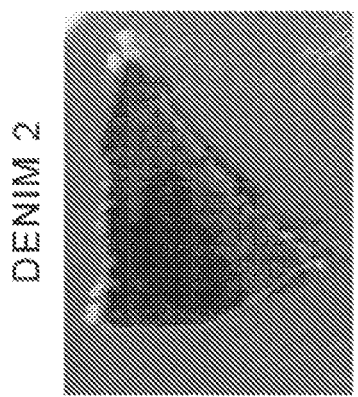
FIG. 5A CEMENT
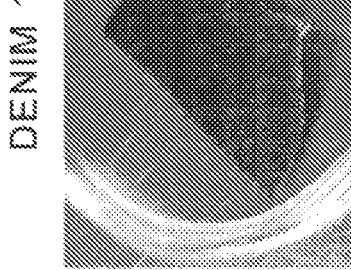
FIG. 5B DENIM 1
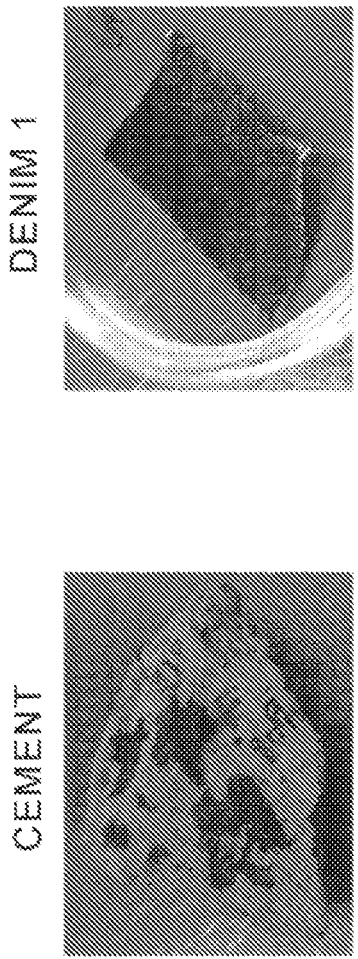
FIG. 5C DENIM 2
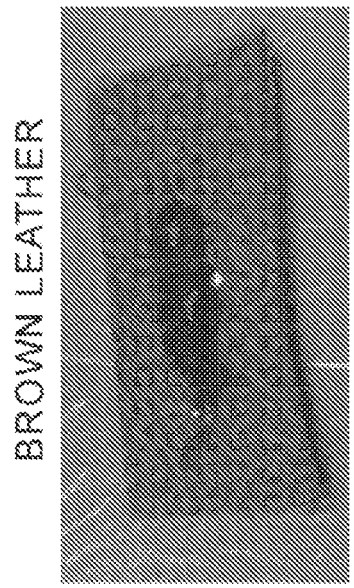
FIG. 5E BROWN LEATHER
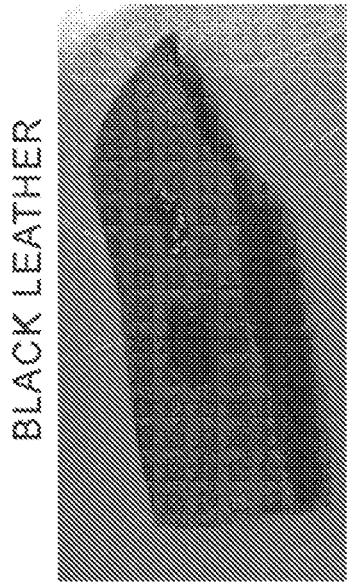
FIG. 5D BLACK LEATHER

DIRECT QUANTIFICATION OF UNPROCESSED NUCLEIC ACID SAMPLES

CROSS-REFERENCE TO RELATED APPLICATIONS

This application is a division of U.S. application Ser. No. 16/403,012 filed May 3, 2019, now U.S. Pat. No. 10,968,476 with issue date Apr. 6, 2021, which is a continuation of U.S. application Ser. No. 15/029,088 filed Apr. 13, 2016, now abandoned, which is a U.S. National Stage application under § 371 of PCT/US2014/055602 filed Sep. 15, 2014, which is a continuation of U.S. application Ser. No. 14/056,921 filed Oct. 17, 2013, now abandoned. The entire contents of the aforementioned applications are incorporated by reference herein.

BACKGROUND

The increasing acceptance of the power of DNA technology for solving crimes has dramatically increased the demand for DNA analysis. Law enforcement agencies, which used to collect DNA evidence only in violent crimes, such as homicide and sexual assault, have begun to collect DNA evidence from property crime cases to aid in their investigation. However, biological evidence samples from property crimes are mostly touch DNA samples. Unlike blood or saliva stains, touch DNA is not always identifiable by eye. In many cases law enforcement officers swab surfaces at a crime scene which they believe have been touched by a perpetrator or collect evidentiary items which they believe has had physical contact with the perpetrator. Therefore, it is understandable that some samples collected this way may not contain any DNA at all. Even when DNA from a perpetrator is collected on a swab, there is no guarantee it will contain enough DNA to obtain a probative DNA profile.

Depending on the nature of the crime, a forensic case may include multiple blood, saliva stain and touch DNA samples. Although short tandem repeat (STR) DNA profiling technology is very powerful, it is also expensive, time consuming and labor intense to process casework samples. Subjecting samples which do not contain sufficient DNA to the full STR DNA typing analysis is a tremendous waste of the already limited resources of forensic laboratories.

Real-time Polymerase Chain Reaction (rtPCR) quantification of forensic samples was originally included in DNA profile workflow to ensure that the optimal amount of DNA was used in the multiplex PCR utilized in DNA profiling. The most advanced available real-time quantification assays also provide information on gender, male/female DNA quantity ratio, expected degree of possible PCR inhibition and level of DNA degradation. The extreme sensitivity of the rtPCR quantification assay also allows the identification of samples that do not have enough DNA for DNA profile analysis.

The input for available real-time quantification assays is an aliquot of a presumptive DNA sample, which has been subjected to extraction and purification procedures. These procedures limit any value of real-time quantification assay as a screening tool, because by the point the sample is ready for real-time quantification analysis, significant time and resources have been spent on extracting and purifying samples which might not have any probative value.

Thus, prior to the instant disclosure a need in the art was for a simple, fast, inexpensive and robust assay which is capable of identifying samples which will be probative. The instant disclosure teaches methods for assaying samples for their probative value without requiring prior extraction and purification. These teachings represent a significant advancement in forensic science.

SUMMARY

The quantization of DNA plays a central role in all applications of forensic DNA analysis. Forensic DNA analysis often involves simultaneously analyzing multiple STRs present in nuclear DNA. In many instances, this is accomplished by utilizing multiplex Polymerase Chain Reaction (PCR). Very discrete windows of input DNA concentration are allowed for the balanced amplification of multiple STRs, thus underlying the importance of DNA quantification prior to STR amplification.

Before the instant disclosure, the input DNA used in the quantification assay was extracted from its source using a variety of methods. These methods include Chelex® extraction, phenol/chloroform, silica membranes, silica-coated beads, ion exchange membranes and magnetic beads with an ionic surface. Problems with such methods include DNA sample loss and they are laborious.

Disclosed herein is a method for directly quantifying the presence of nucleic acids without prior application of extraction techniques, the method encompassing depositing a solid support into a vessel, performing a PCR within the vessel and detecting the level of fluorescence emitted from the vessel, wherein the level of fluorescence is detected by a Charge-coupled Device (CCD). In some embodiments, the solid support is paper. In some embodiments, the solid support is filter paper.

In some embodiments, the PCR is a two-step PCR, wherein the annealing and extension temperatures are the same.

BRIEF DESCRIPTION OF THE DRAWINGS

FIGS. 5A-5E show dry blood stains present on various substrates: (5A) cement; (5B) denim 1; (5C) denim 2; (5D) black leather; and (5E) brown leather.

DETAILED DESCRIPTION

Figure 1:
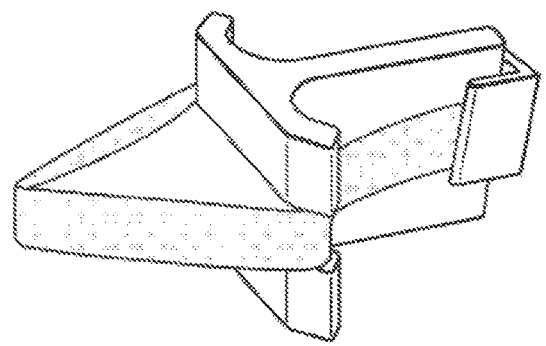
FIG. 1 shows a 5 mm PE-swab.
Figure 2:
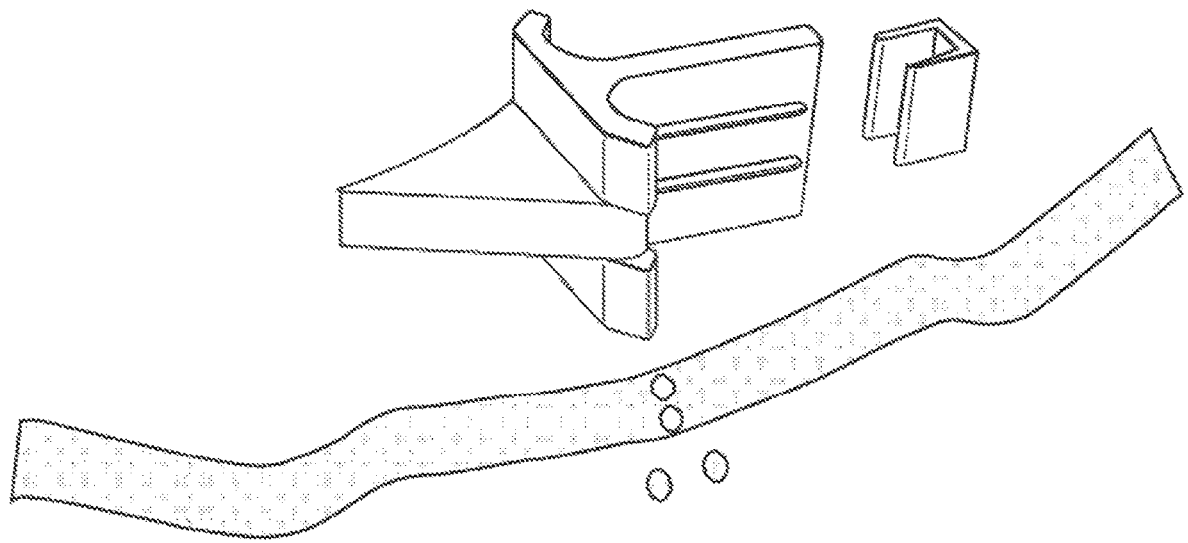
FIG. 2 shows a disassembled 5 mm PE-swab displaying three components of the PE-swab; the filter paper strip, the holder and the clip, as well as two 2 mm punches generated using a HARRIS UNI-CORE™ punch from the sampling area of the PE-swab.
Figure 3A:
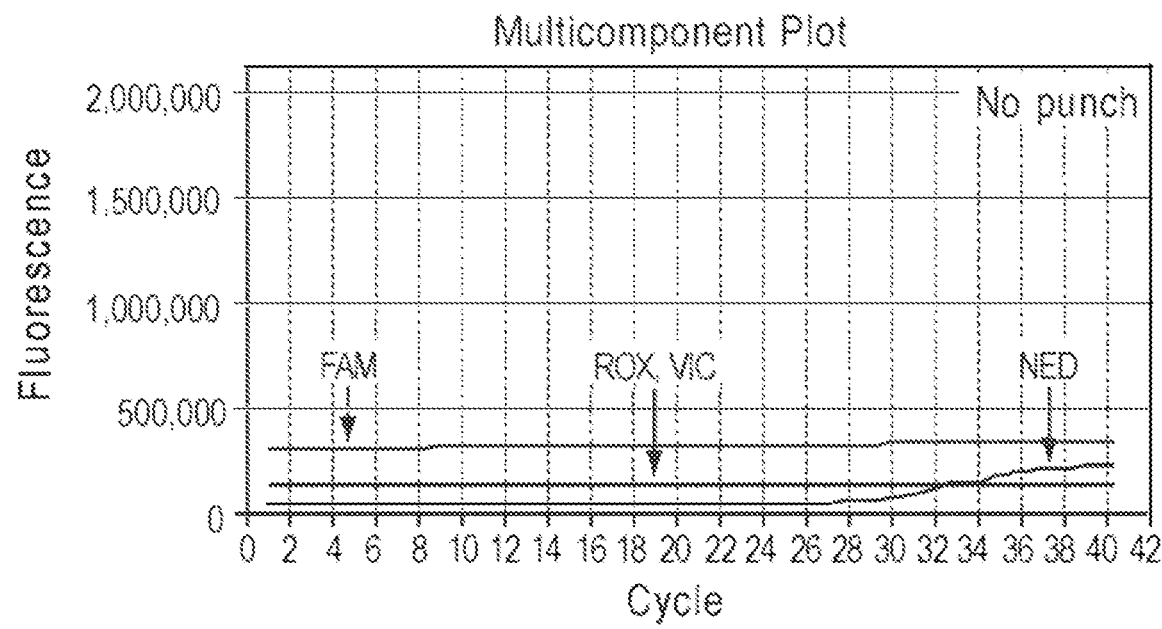
FIGS. 3A-3D show the fluorescent signals collected in different dye channels during an rtPCR with circular filter paper punches with the indicated diameter without added nucleic acid template. A no filter paper control was also included (no punch).
Figure 3B:
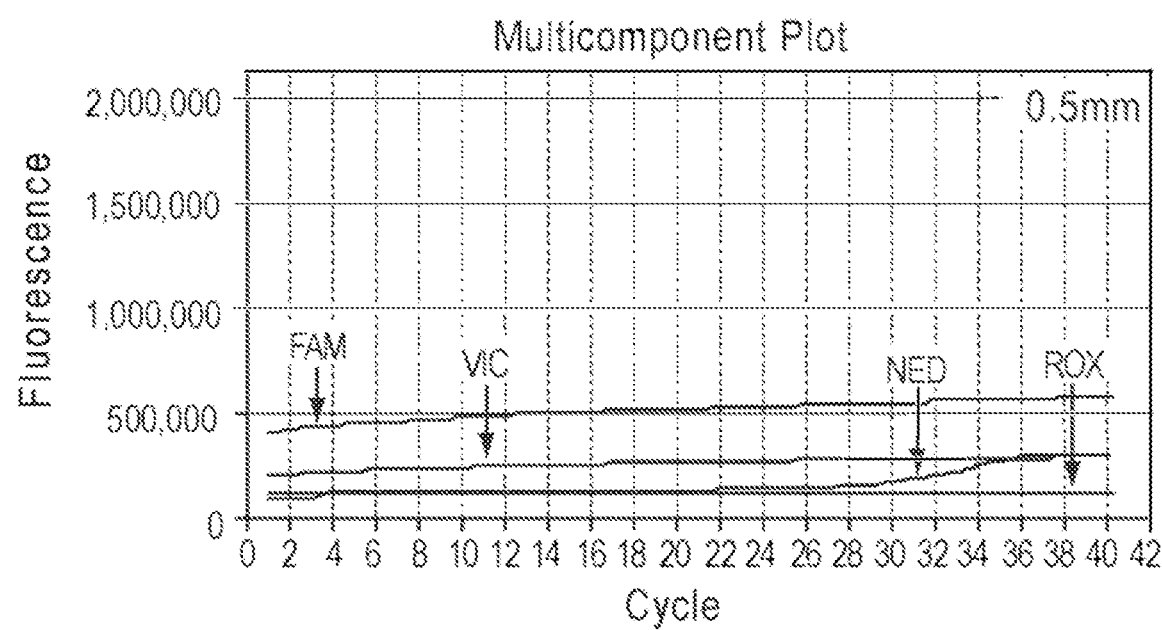
Figure 3C:
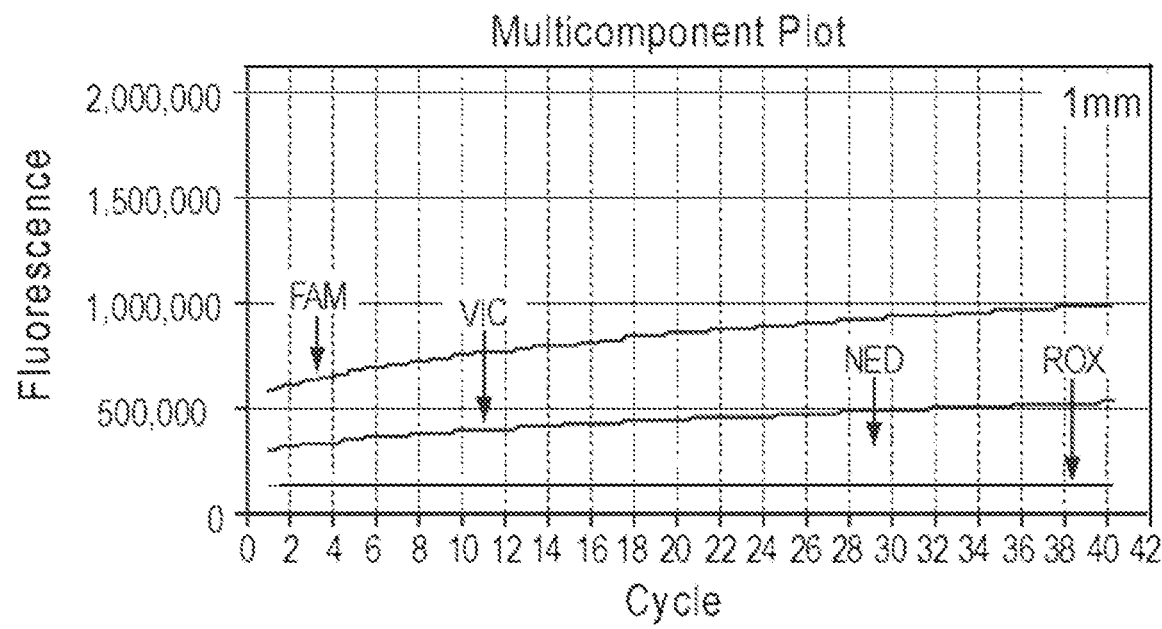
Figure 3D:
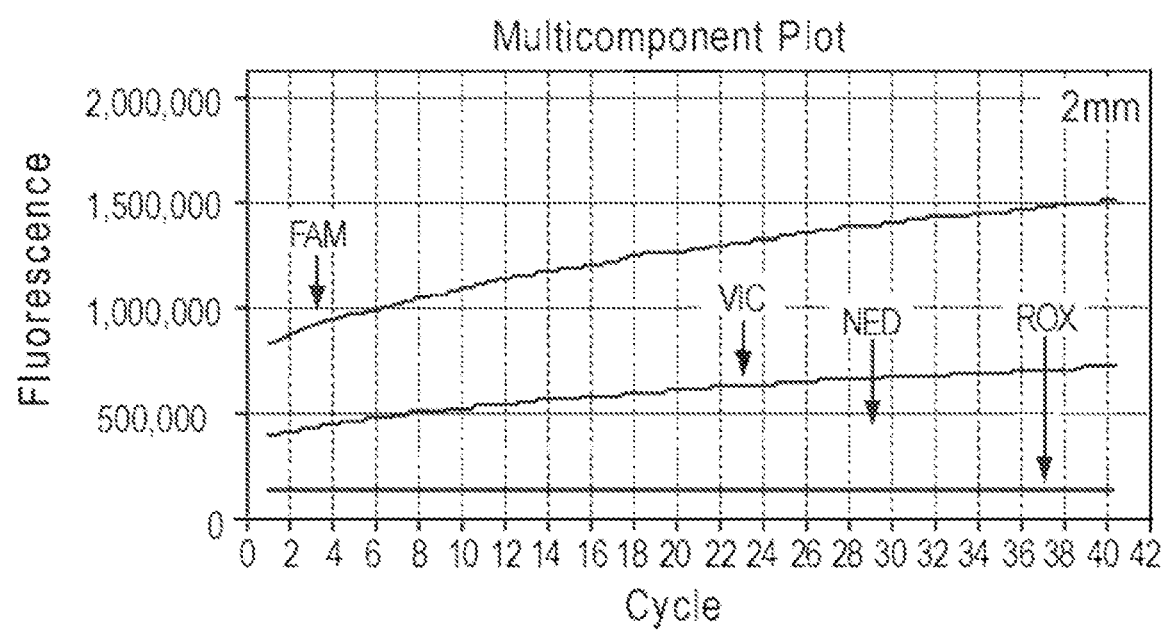

Nucleic acid can be quantified using Polymerase Chain Reaction (PCR) by the detection of amplification products present at the end of PCR, endpoint quantitative PCR, or during PCR, real-time PCR (rtPCR). In rtPCR, fluorescent dyes are generally used to label PCR products during thermal cycling. This allows quantification of the template to be based on the intensity of the fluorescent signal during the exponential phase of amplification; before limiting reagents or the inactivation of the polymerase have started to have an effect on the efficiency of PCR amplification.

In the exponential phase, fluorescent intensity increases proportionally with each amplification cycle. The dominant thinking has been that opaque materials can mask a fluorescent signal and thus they should be excluded from rtPCR reactions.

In contrast to this, and as disclosed herein, it is now shown that solid supports, such as filter paper, can be successfully incorporated into rtPCR. This differs significantly from standard rtPCR protocols wherein nucleic acids are extracted away from a solid support, and this extracted nucleic acid, free of the solid support, is introduced as a substrate for rtPCR.

In forensics, for example, an object thought to have been touched by a suspect is contacted with filter paper to collect any residual nucleic acid left by the suspect on the object. Prior to rtPCR, the filter paper is subjected to extraction techniques used to remove any nucleic acids from the filter paper. The resulting extracted nucleic acids are then introduced into the rtPCR for quantification, with the filter paper being separately discarded. This differs from the instant disclosure wherein the solid support, such as filter paper, is introduced directly into the rtPCR. This new methodology disclosed herein is referred to as "direct quantification."

Accordingly, in some embodiments, a method encompassing depositing a solid support into a vessel, performing a PCR within the vessel in the presence of the solid support, and detecting the level of fluorescence emitted from the vessel while PCR is on-going, wherein the level of fluorescence is detected by a charge-coupled device is disclosed. In some embodiments, the level of fluorescence detected is related to the quantity of the nucleic acid present.

"Solid support" refers to any solid surface to which nucleic acids can be attached. In some embodiments the solid support is opaque.

Accordingly, in some embodiments, a method is disclosed encompassing depositing a solid support into a vessel, performing a PCR within the vessel in the presence of the solid support, and detecting the level of fluorescence emitted from the vessel while PCR is on-going, wherein the level of fluorescence is detected by a charge-coupled device is disclosed and the solid support is opaque.

In some embodiments, the solid support has a surface area approximately the same as that of a circle with a diameter of about 3 mm. In some embodiments, the solid support has a surface area approximately the same as that of a circle with a diameter of about 2 mm. In some embodiments, the solid support has a surface area approximately the same as that of a circle with a diameter of about 1 mm. In some embodiments, the solid support has a surface area approximately the same as that of a circle with a diameter of about 0.75 mm.

In some embodiments, the solid support is approximately circular in shape, sometimes referred to as a punch, with a diameter of about 3 mm. In some embodiments, the solid support is approximately circular in shape, with a diameter of about 2 mm. In some embodiments, the solid support is approximately circular in shape, with a diameter of about 1 mm. In some embodiments, the solid support is approximately circular in shape, with a diameter of about 0.75 mm.

In some embodiments, a method is disclosed encompassing depositing a solid support into a vessel, performing a PCR within the vessel and detecting the level of fluorescence emitted from the vessel, wherein the level of fluorescence is detected by a charge-coupled device, wherein the solid support is paper.

"Paper" refers to sheet-like masses and molded products containing cellulosic fibers. Cellulosic fibers can include digested fibers from softwood (derived from coniferous trees), hardwood (derived from deciduous trees) or cotton linters. Fibers from Esparto grass, bagasse, kemp, flax, and other lignaceous and cellulosic fiber sources may also be utilized.

In some embodiments, a method is disclosed encompassing depositing a solid support into a vessel, performing PCR within the vessel and detecting the level of fluorescence emitted from the vessel while PCR is on-going, wherein the level of fluorescence is detected by a charge-coupled device, wherein the solid support is filter paper. In some embodiments, the filter paper is Whatman 903. In some embodiments, the filter paper is Ahlstrom grade 226. In some embodiments, the filter paper is Munktell TFN.

In some embodiments, a weak base is sorbed to the filter paper before depositing the filter paper into the vessel. A "weak base" refers to a base which has a pH of about 6 to 10, preferably about pH 8 to 9.5. One function of the weak base may be to act as a buffer to maintain a composition pH of about 6 to 10, preferably about pH 8.0 to 9.5, for example, pH 8.6, Hence, a weak base suitable may, in conjunction with other components, provide a pH of 6 to 10, preferably, about pH 8.0 to 9.5. Weak bases include organic and inorganic bases. Examples of inorganic weak bases include, for example, an alkali metal carbonate, bicarbonate, phosphate or borate (For example, sodium, lithium, or potassium carbonate). Organic weak bases include, for example, trishydroxyrmethyl amino methane (Tris), ethanolamine, triethanolamine and glycine and alkaline salts of organic acids (for example, trisodium citrate). The weak base may be either a free base or a salt, for example, a carbonate salt.

In some embodiments, a chelating agent is sorbed to the filter paper before depositing the filter paper into the vessel. A "chelating agent" refers any compound capable of complexing multivalent ions including Group II and Group III multivalent metal ions and transition metal ions (for example, Cu, Fe, Zn, Mn, etc.). Ethylene diamine tetraacetic acid (EDTA) is an example of a chelating agent. Chelating agents such as a citrate or oxalate can also be applied to the filter paper.

In some embodiments, a detergent is sorbed to the filter paper before depositing the filter paper into the vessel. "Detergent" includes ionic detergents, preferably anionic detergents. A preferred anionic detergent may have a hydrocarbon moiety, such as an aliphatic or aromatic moiety, and one or more anionic groups. Particularly preferred anionic detergents include sodium dodecyl sulphate (SDS) and sodium lauryl sarcosinate (SLS).

In some embodiments, a weak base, a chelating agent and a detergent are sorbed to the filter paper before depositing the filter paper into the vessel. In some embodiments, the filter paper is FTA™.

In some embodiments, a method is disclosed encompassing depositing a solid support into a vessel, performing a rtPCR within the vessel and detecting the level of fluorescence emitted from the vessel while rtPCR is on-going, wherein the level of fluorescence is detected by a charge-coupled device, wherein the solid support is a non-cellulosic fiber.

A "non-cellulosic fiber" refers to a polymeric material characterized by having hydroxyl groups attached to the polymer backbone, for example glass fibers and synthetic fibers modified with hydroxyl groups. Other fibrous materials include synthetic fibers, such as rayon, polyethylene and polypropylene can also be utilized in combination with natural cellulosic fibers or other fibers containing hydroxyl groups. Mixtures of any of the foregoing fibers may be used.

A "vessel" indicates any container or holder wherein the methods disclosed herein can occur.

In some embodiments, a method encompassing depositing a solid support into a vessel, performing a multiplex rtPCR within the vessel and detecting the level of fluorescence emitted from the vessel while rtPCR is on-going, wherein the level of fluorescence is detected by a charge-coupled device is disclosed.

"Multiplex PCR" refers to the simultaneous amplification of more than one target polynucleotide in a vessel. In some embodiments, at least 2 targets are amplified simultaneously. In some embodiments, at least 3 targets are amplified simultaneously. In other embodiments, at least 4 targets are amplified simultaneously. In still other embodiments, at least 5 targets are amplified simultaneously. In other embodiments, at least 6 targets are amplified simultaneously. In some embodiments, 7 or more targets are amplified simultaneously.

"Target" refers to a nucleic acid sequence to be amplified. Copies of the target sequence which are generated during the amplification reaction are referred to as amplification products, amplimers, or amplicons. A target nucleic acid may be composed of segments of a chromosome, a complete gene with or without intergenic sequence, segments or portions of a gene, with or without intergenic sequence. Target nucleic acids may include a wild-type sequence(s), a mutation, deletion or duplication, tandem repeat regions, a gene of interest, a region of a gene of interest or any upstream or downstream region thereof. Target nucleic acids may represent alternative sequences or alleles of a particular gene. Target nucleic acids may be derived from genomic DNA, cDNA, or RNA. A target nucleic acid may be DNA or RNA from a eukaryotic cell or a nucleic acid copied or amplified therefrom but not a prokaryotic cell or virus. A target nucleic acid may be DNA or RNA from a prokaryotic cell or a nucleic acid copied or amplified therefrom but not a eukaryotic cell or virus. A target nucleic acid may be DNA or RNA from a virus, wherein the virus is not cytomegalovirus.

In some embodiments, a method encompassing depositing a solid support into a vessel, performing a rtPCR within the vessel and detecting the level of fluorescence emitted from the vessel while rtPCR is on-going, wherein the level of fluorescence is detected by a charge-coupled device is disclosed and wherein the target template for the PCR in the vessel is a nucleic acid, wherein the target nucleic acid is not a cytomegalovirus nucleic acid.

In some embodiments, a method encompassing depositing a solid support into a vessel, performing a rtPCR within the vessel and detecting the level of fluorescence emitted from the vessel while rtPCR is on-going, wherein the level of fluorescence is detected by a charge-coupled device is disclosed and wherein the target template for the PCR in the vessel is a eukaryotic nucleic acid.

In some embodiments, a method encompassing depositing a solid support into a vessel, performing a rtPCR within the vessel and detecting the level of fluorescence emitted from the vessel while rtPCR is on-going, wherein the level of fluorescence is detected by a charge-coupled device is disclosed and wherein the target template for the PCR in the vessel is a prokaryotic nucleic acid.

In some embodiments, a method encompassing depositing a solid support into a vessel, performing a rtPCR within the vessel and detecting the level of fluorescence emitted from the vessel while rtPCR is on-going, wherein the level of fluorescence is detected by a charge-coupled device is disclosed and wherein the target template for the rtPCR in the vessel is a virus nucleic acid, wherein the virus nucleic acid is not cytomegalovirus.

In some embodiments, a method encompassing depositing a solid support into a vessel, performing a multiplex rtPCR within the vessel and detecting the level of fluorescence emitted from the vessel while rtPCR is on-going, wherein the level of fluorescence is detected by a charge-coupled device is disclosed and wherein at least one target template for the rtPCR in the vessel is a eukaryotic nucleic acid.

In some embodiments, a method encompassing depositing a solid support into a vessel, performing a multiplex rtPCR within the vessel and detecting the level of fluorescence emitted from the vessel while rtPCR is on-going, wherein the level of fluorescence is detected by a charge-coupled device is disclosed and wherein at least one target template for the rtPCR in the vessel is a prokaryotic nucleic acid.

In some embodiments, a method encompassing depositing a solid support into a vessel, performing a multiplex rtPCR within the vessel and detecting the level of fluorescence emitted from the vessel while rtPCR is on-going, wherein the level of fluorescence is detected by a charge-coupled device is disclosed and wherein at least one target template for the rtPCR in the vessel is a virus nucleic acid.

In some embodiments, a method encompassing depositing a solid support into a vessel, performing a multiplex rtPCR within the vessel and detecting the level of fluorescence emitted from the vessel while rtPCR is on-going, wherein the level of fluorescence is detected by a charge-coupled device is disclosed and wherein at least one target template for the rtPCR in the vessel is a eukaryotic nucleic acid but not a prokaryotic or viral nucleic acid.

In some embodiments, a method encompassing depositing a solid support into a vessel, performing a multiplex rtPCR within the vessel and detecting the level of fluorescence emitted from the vessel while rtPCR is on-going, wherein the level of fluorescence is detected by a charge-coupled device is disclosed and wherein at least one target template for the rtPCR in the vessel is a prokaryotic nucleic acid but not a eukaryotic or viral nucleic acid.

In some embodiments, a method encompassing depositing a solid support into a vessel, performing a multiplex rtPCR within the vessel and detecting the level of fluorescence emitted from the vessel while rtPCR is on-going, wherein the level of fluorescence is detected by a charge-coupled device is disclosed and wherein at least one target template for the rtPCR in the vessel is a viral nucleic acid but not a prokaryotic or eukaryotic nucleic acid.

In some embodiments, a method encompassing depositing a solid support into a vessel, performing a rtPCR within the vessel and detecting the level of fluorescence emitted from the vessel while rtPCR is on-going, wherein the level of fluorescence is detected by a charge-coupled device is disclosed and wherein the target template for the rtPCR in the vessel is a nucleic acid, wherein the target nucleic acid is a synthetic nucleic acid.

A "synthetic nucleic acid" is a nucleic acid whose nucleotide sequence is designed without reference to a nucleic acid sequence of a eukaryote, prokaryote or virus. A nucleic acid sequence synthesized with random sequence order by an oligonucleotide synthesis machine would be an example of a synthetic nucleic acid. The Internal PCR Control (IPC) included in the QUANTIFILER® DUO DNA Quantification kit is a synthetic nucleic acid.

In some embodiments, a method encompassing depositing a solid support into a vessel, performing a multiplex rtPCR within the vessel and detecting the level of fluorescence emitted from the vessel while rtPCR is on-going, wherein the level of fluorescence is detected by a charge-coupled device is disclosed and wherein at least one target template for the rtPCR in the vessel is a eukaryotic nucleic acid and a synthetic nucleic acid.

In some embodiments, a method encompassing depositing a solid support into a vessel, performing a multiplex rtPCR within the vessel and detecting the level of fluorescence emitted from the vessel while rtPCR is on-going, wherein the level of fluorescence is detected by a charge-coupled device is disclosed and wherein at least one target template for the rtPCR in the vessel is a prokaryotic nucleic acid and a synthetic nucleic acid.

In some embodiments, a method encompassing depositing a solid support into a vessel, performing a multiplex rtPCR within the vessel and detecting the level of fluorescence emitted from the vessel while rtPCR is on-going, wherein the level of fluorescence is detected by a charge-coupled device is disclosed and wherein at least one target template for the rtPCR in the vessel is a viral nucleic acid and a synthetic nucleic acid.

In some embodiments, a method encompassing depositing a solid support into a vessel, performing a multiplex rtPCR within the vessel and detecting the level of fluorescence emitted from the vessel while rtPCR is on-going, wherein the level of fluorescence is detected by a charge-coupled device is disclosed and wherein at least one target template for the rtPCR in the vessel is a synthetic nucleic acid but not a prokaryotic or viral nucleic acid.

In some embodiments, a method is disclosed encompassing contacting a solid support to a surface in the collection of evidence for a criminal investigation, depositing the solid support into a vessel, performing a rtPCR within the vessel and detecting the level of fluorescence emitted from the vessel while rtPCR is on-going, wherein the level of fluorescence is detected by a charge-coupled device.

In some embodiments, a method is disclosed encompassing contacting a paper to a surface in the collection of evidence for a criminal investigation, depositing the paper into a vessel, performing a rtPCR within the vessel and detecting the level of fluorescence emitted from the vessel while rtPCR is on-going, wherein the level of fluorescence is detected by a charge-coupled device.

"Criminal investigation" refers to any action which could result in the filing of a criminal charge.

In some embodiments, a method is disclosed encompassing contacting a solid support to a biological sample, depositing the solid support into a vessel, performing a rtPCR within the vessel and detecting the level of fluorescence emitted from the vessel while rtPCR is on-going, wherein the level of fluorescence is detected by a charge-coupled device.

A "biological sample" refers to a collection made from an organism such as a eukaryote, prokaryote or virus.

In some embodiments, a method is disclosed encompassing contacting a solid support to a specimen, depositing the solid support into a vessel, performing a multiplex rtPCR within the vessel and detecting the level of fluorescence emitted from the vessel while rtPCR is on-going, wherein the level of fluorescence is detected by a charge-coupled device.

A "specimen" refers to whole blood, plasma, serum, saliva, sweat, vaginal secretions, semen, tissues, urine, cerebrospinal fluid and touch nucleic acid. "Touch nucleic acid" or "transfer nucleic acid" refers to nucleic acid that may be left on a surface after being contacted by an organism. For example, a fingerprint can contain nucleic acid and represents a touch nucleic acid.

In some embodiments, a method is disclosed encompassing contacting a solid support to a specimen, depositing the solid support into a vessel, performing a rtPCR within the vessel and detecting the level of fluorescence emitted from the vessel while rtPCR is on-going, wherein the level of fluorescence is detected by a charge-coupled device, wherein the specimen is whole blood.

In some embodiments, a method is disclosed encompassing contacting a solid support to a specimen, depositing the solid support into a vessel, performing a rtPCR within the vessel and detecting the level of fluorescence emitted from the vessel, wherein the level of fluorescence is detected by a charge-coupled device, wherein the specimen is urine.

In some embodiments, a method is disclosed encompassing contacting a solid support to a specimen, depositing the solid support into a vessel, performing a rtPCR within the vessel and detecting the level of fluorescence emitted from the vessel while rtPCR is on-going, wherein the level of fluorescence is detected by a charge-coupled device and wherein the specimen is not urine.

In some embodiments, a method is disclosed encompassing contacting a solid support to a specimen, depositing the solid support into a vessel, performing a rtPCR within the vessel and detecting the level of fluorescence emitted from the vessel, wherein the level of fluorescence is detected by a charge-coupled device, wherein the specimen is touch DNA. In some embodiments, the touch DNA is a fingerprint.

In some embodiments, a method is disclosed encompassing contacting a solid support to a specimen, depositing the solid support into a vessel, performing a multiplex rtPCR within the vessel and detecting the level of fluorescence emitted from the vessel while rtPCR is on-going, wherein the level of fluorescence is detected by a charge-coupled device.

In some embodiments, a method is disclosed encompassing contacting a solid support to a specimen, depositing the solid support into a vessel, performing a multiplex rtPCR within the vessel and detecting the level of fluorescence emitted from the vessel while rtPCR is on-going, wherein the level of fluorescence is detected by a charge-coupled device, wherein the specimen is whole blood.

In some embodiments, a method is disclosed encompassing contacting a solid support to a specimen, depositing the solid support into a vessel, performing a multiplex rtPCR within the vessel and detecting the level of fluorescence emitted from the vessel while rtPCR is on-going, wherein the level of fluorescence is detected by a charge-coupled device, wherein the specimen is urine.

In some embodiments, a method is disclosed encompassing contacting a solid support to a specimen, depositing the solid support into a vessel, performing a multiplex rtPCR within the vessel and detecting the level of fluorescence emitted from the vessel while rtPCR is on-going, wherein the level of fluorescence is detected by a charge-coupled device, wherein the specimen is touch DNA. In some embodiments, the touch DNA is a fingerprint.

In some embodiments, a method is disclosed encompassing contacting a solid support to a surface, depositing the solid support into a vessel, depositing at least one primer pair into the vessel, performing a rtPCR within the vessel and detecting the level of fluorescence emitted from the vessel while rtPCR is on-going, wherein the amplicon produced by at least one primer pair is a replicate of eukaryotic nucleic acid, and wherein the level of fluorescence is detected by a charge-coupled device.

In some embodiments, a method is disclosed encompassing contacting a solid support to a surface, depositing the solid support into a vessel, depositing at least one primer pair into the vessel, performing a rtPCR within the vessel and detecting the level of fluorescence emitted from the vessel while rtPCR is on-going, wherein the amplicon produced by the at least one primer pair is a replicate of prokaryotic nucleic acid, and wherein the level of fluorescence is detected by a charge-coupled device.

In some embodiments, a method is disclosed encompassing contacting a solid support to a surface, depositing the solid support into a vessel, depositing at least one primer pair into the vessel, performing a rtPCR within the vessel and detecting the level of fluorescence emitted from the vessel while rtPCR is on-going, wherein the amplicon produced by the at least one primer pair is a replicate of viral nucleic acid wherein the level of fluorescence is detected by a charge-coupled device and wherein the viral nucleic acid is not cytomegalovirus.

In some embodiments, a method is disclosed encompassing contacting a solid support to a surface, depositing the solid support into a vessel, depositing at least one primer pair into the vessel, performing a multiplex rtPCR within the vessel and detecting the level of fluorescence emitted from the vessel while rtPCR is on-going, wherein the amplicon produced by at least one primer pair is a replicate of eukaryotic nucleic acid, and wherein the level of fluorescence is detected by a charge-coupled device.

In some embodiments, a method is disclosed encompassing contacting a solid support to a surface, depositing the solid support into a vessel, depositing at least one primer pair into the vessel, performing a multiplex rtPCR within the vessel and detecting the level of fluorescence emitted from the vessel while rtPCR is on-going, wherein the amplicon produced by the at least one primer pair is a replicate of prokaryotic nucleic acid, and wherein the level of fluorescence is detected by a charge-coupled device.

In some embodiments, a method is disclosed encompassing contacting a solid support to a surface, depositing the solid support into a vessel, depositing at least one primer pair into the vessel, performing a multiplex rtPCR within the vessel and detecting the level of fluorescence emitted from the vessel while rtPCR is on-going, wherein the amplicon produced by the at least one primer pair is a replicate of viral nucleic acid wherein the level of fluorescence is detected by a charge-coupled device and wherein the viral nucleic acid.

"Primer(s)" refer to isolated oligonucleotides that can anneal to a complementary nucleic acid strand and can be extended, for example by a polymerase. A primer pair refers to two primers that anneal to opposite strands of a DNA target.

There is largely a quantitative relationship between the starting amount of a target and the amount of amplicons produced. rtPCR detects the accumulation of amplicons during the amplification reaction. A number of ways are employed to detect PCR products in an rtPCR assay. These include non-specific double strand intercalating dyes, such as SYBR® Green, and probe based techniques which have the advantage of not binding to confounding molecules like primer-dimers.

A "probe(s)" refers an isolated oligonucleotide to which may be attached a detectable label or reporter molecule.

Examples of probe based technologies employed in rtPCR assays include 5'-exonuclease, molecular beacons, hybridization probes and Scorpion probes.

The 5'-exonuclease (TAQMAN™) probes are oligonucleotides that contain fluorophore and quencher moieties preferably located on 5' and 3' termini. Very little fluorescence is emitted from intact probe due to efficient intra-molecular quenching. However, during PCR amplification, the probe specifically hybridizes to its target sequence and the 5'-3'-exonuclease activity of Taq polymerase cleaves the probe between fluorophore and quencher moieties. Enzymatic cleavage of TAQMAN™ probes spatially separates fluorophore and quencher components, causing significant increases in fluorescence emission correlated with target amplification.

"Fluorophore" refers to a moiety that is inherently fluorescent or demonstrates a change in fluorescence upon binding to a biological compound or metal ion, or when metabolized by an enzyme. Numerous fluorophores are known, examples of which include coumarins, acridines, furans, dansyls, cyanines, pyrenes, naphthalenes, benzofurans, quinolines, quinazolinones, indoles, benzazoles, borapolyazaindacenes, oxazines and xanthenes, with the latter including fluoresceins, rhodamines, rosamines and rhodols.

"Quencher" refers to any fluorescent-modifying moiety that can attenuate at least partly the light emitted by a fluorophore. This attenuation is referred to as "quenching." The excitation of a fluorophore in the presence of the quenching group leads to an emission signal that is less intense than expected, or even completely absent. Quenching typically occurs through energy transfer between the excited fluorophore and the quenching group.

Molecular beacons are single-stranded oligonucleotide probes that are non-fluorescent in isolation, but become fluorescent upon hybridization to target sequences. Non-hybridized molecular beacons form stem-loop structures, possessing a fluorophore covalently linked to one end of the molecule and a quencher linked to the other, such that the hairpin of the beacon places the fluorophore moiety in close proximity with the quencher. When molecular beacons hybridize to target sequences, fluorophore and quencher moieties become spatially separated, such that the fluorophore is no longer quenched and the molecular beacon fluoresces. The secondary structure of the molecular beacon conveys high specificity to the hybridization probe.

Hybridization probes are oligonucleotides that are singly labeled with a fluorophore moiety. Two such oligonucleotides are required for each hybridization probe assay, one labeled with a donor fluorophore and the other with an acceptor fluorophore. Fluorescein is commonly employed as the donor and CY5™, LC RED® 640 and LC RED®705 are commonly used as acceptors. Excitation of the donor fluorophore produces an emission spectrum that overlaps with the absorption spectrum of the acceptor fluorophore. Hybridization probe pairs are designed to recognize adjacent nucleotide sequences within target molecules. In isolation, the acceptor oligonucleotide is not excited and does not generate a fluorescent signal. However, during hybridization to polynucleotide target sequences, the donor and acceptor probes are brought into close proximity, allowing fluorescence resonance energy transfer from the donor to the acceptor. Fluorescent signal from the acceptor fluorophore is only emitted when both probes are hybridized to the target molecule. When incorporated into PCR reactions, fluorescence from the acceptor probe is monitored once per cycle of amplification, to facilitate real-time measurement of product accumulation, where the amount of fluorescence emitted by the acceptor is proportional to the quantity of target synthesized.

5'-exonuclease, molecular beacon and hybridization probe assays are bimolecular systems that have the probe and target sequences located on separate DNA strands. Scorpion probes operate through single molecular binding events, where the probe and amplified target sequence are located on the same DNA strand. Single molecular binding events are kinetically favored over bimolecular hybridization. Scorpion probes comprise a primer with an attached probe tail sequence, where the probe sequence is contained within a stem-loop secondary structure similar to that of a molecular beacon. In the non-extended form, Scorpion primers are non-fluorescent due to fluorophore and quencher moieties being in close proximity. During PCR, the primer component of the Scorpion is extended at its 3' end producing the homologous target sequence required for probe hybridization. When the Scorpion probe sequence hybridizes to amplified target the fluorophore and quencher moieties become spatially separated generating significant increases in fluorescent signal concurrent with target amplification.

A number of fluorescent dyes can be detected in a rtPCR assay and can include, without limitation, the following: 5- or 6-carboxyfluorescein (FAM™), VIC™, NED™, fluorescein, fluorescein isothiocyanate (FITC), IRD-700/800, cyanine dyes, such as CY3™, CY5™, CY3.5™, CY5.5™ Cy7™ xanthen, 6-carboxy-2',4',7',4,7-hexachlorofluorescein (HEX), 6-carboxy-1,4-dichloro-2',7'-dichloro-fluorescein (TET®), 6-carboxy-4',5'-dichloro-2',7'-dimethodyfluorescein (JOE™), N,N,N',N'-tetramethyl-6-carboxyrhodamine (TAMRA™), 6-carboxy-X-rhodamine (ROX), 5-carboxyrhodamine-6G (R6G5), 6-carboxyrhodamine-6G (RG6), rhodamine, rhodamine green, rhodamine red, rhodamine 110, Rhodamin 6G®, BODIPY dyes, such as BODIPY TMR, oregon green, coumarines, such as umbelliferone, benzimides, such as Hoechst 33258; phenanthridines, such as TEXAS RED®, CALIFORNIA RED®, YAKIMA YELLOW, ALEXA FLUOR® 350, ALEXA FLUOR® 405, ALEXA FLUOR® 430, ALEXA FLUOR® 488, ALEXA FLUOR® 500, ALEXA FLUOR® 514, ALEXA FLUOR®532, ALEXA FLUOR® 546, ALEXA FLUOR® 555, ALEXA FLUOR® 568, ALEXA FLUOR® 594, ALEXA FLUOR® 610, ALEXA FLUOR® 633, ALEXA FLUOR® 647, ALEXA FLUOR® 660, ALEXA FLUOR® 680, ALEXA FLUOR® 700, ALEXA FLUOR® 750, PET®, ethidium bromide, acridinium dyes, carbazol dyes, phenoxazine dyes, porphyrine dyes, polymethin dyes, Atto 390, Atto 425, Atto 465, Atto 488, Atto 495, Atto 520, Atto 532, Atto 550, Atto 565, Atto 590, Atto 594, Atto 620, Atto 633, Atto 647N, Atto 655, Atto RhoG6, Atto Rhol 1, Atto Rhol2, Atto Rhol01, BMN™-5, BMN™-6, CEQ8000 D2, CEQ8000 D3, CEQ8000 D4, DY-480XL, DY-485XL, DY-495, DY-505, DY-510XL, DY-521XL, DY-521XL, DY-530, DY-547, DY-550, DY-555, DY-610, DY-615, DY-630, DY-631, DY-633, DY-635, DY-647, DY-651, DY-675, DY-676, DY-680, DY-681, DY-700, DY-701, DY-730, DY-731, DY-732, DY-750, DY-751, DY-776, DY-780, DY-781, DY-782, CAL FLUOR® Gold 540, CAL FLUORRED 590, CAL FLUOR Red 610, CAL FLUORRed 635, IRDye® 700Dx, IRDye® 800CW, MARINA BLUE®, PACIFIC BLUE®, YAKIMA YELLOW®, 6-(4,7-Dichloro-2',7'-diphenyl-3',6'-dipivaloylfluorescein-6-carboxamido)-hexyl-1-0-(2-cyanoethyl)-(N,N-diisopropyl)-phosphoramidite (SIMA), CAL FLUOR® Gold 540, CAL FLUOR® Orange 560, CAL FLUOR Red 635, Quasar 570, Quasar 670, LIZ, Sunnyvale Red, LC RED® 610, LC RED® 640, LC RED®670 and LC RED®705.

The fluorescent signal emitted from the vessel during the rtPCR can be detected using a number of different types of detectors including Charge-coupled Device (CCD), photodiode and photomultiplier tube. A CCD converts the light that it captures into digital data. The quality of the image captured is determined by the resolution, usually expressed in terms of megapixels. CCDs are typically used to capture an image of a vessel or reaction plate, whose content is then interpreted by instrument software.

A photodiode is a type of photodetector that, when exposed to light, causes a current to flow. A photomultiplier tube multiplies the current that is produced by incident light.

Accordingly, in some embodiments, a method encompassing depositing a solid support into a vessel, performing a rtPCR within the vessel and detecting the level of fluorescence emitted from the vessel while rtPCR is on-going, wherein the level of fluorescence is detected by a charge-coupled device but not a photodiode or photomultiplier is disclosed.

In some embodiments, a method encompassing depositing a solid support into a vessel, performing a rtPCR within the vessel and detecting the level of fluorescence emitted from the vessel while rtPCR is on-going, wherein the level of fluorescence is detected by a charge-coupled device or a photodiode but not a photomultiplier is disclosed.

In some embodiments, a method encompassing depositing a solid support into a vessel, performing a multiplex rtPCR within the vessel and detecting the level of fluorescence emitted from the vessel while rtPCR is on-going, wherein the level of fluorescence is detected by a charge-coupled device, a photodiode or a photomultiplier is disclosed.

In some embodiments, a method encompassing depositing a solid support into a vessel, performing a multiplex rtPCR within the vessel and detecting the level of fluorescence emitted from the vessel while rtPCR is on-going, wherein the level of fluorescence is detected by a charge-coupled device or a photodiode but not a photomultiplier is disclosed.

In some embodiments, a method encompassing depositing a solid support into a vessel, performing a multiplex rtPCR within the vessel and detecting the level of fluorescence emitted from the vessel while rtPCR is on-going, wherein the level of fluorescence is detected by a charge-coupled device but not a photomultiplier or a photodiode is disclosed.

EXAMPLES

A PE Swab Sample Collector

An example of a PE swab for collecting samples for analysis is depicted in FIG. 1. A PE-swab was assembled by wrapping the filter paper strip around the holder and then secured the paper strip on the holder by the clip at the end of PE-swab handle. The width of the active sampling area is defined by the angled fold of the holder. In the example shown in FIG. 1, the PE-swab is about 40 mm long when measured from the active sampling area to the end of the swab handle. The active sampling area is about 5 mm in this example. The PE-swab handle is about 15 mm wide.

The active sampling area of a 5 mm PE-swab is about 1 mm×5 mm. After removing a 0.5 mm punch, four 1 mm punches can be practically generated from the remaining active sampling area of a 5 mm PE-swab.

In some instances, a liquid is applied to a surface to facilitate sample collection by swabbing.

After swabbing, the filter paper strip was detached from the holder. Using a HARRIS UNI-CORE™ punch (Ted Pella, Inc.), punches of desired size were generated from the active sampling area of the filter paper for direct real time PCR (rtPCR) assay or direct STR PCR. If a swabbing liquid was used, the filter paper was dried prior to punching.

The Effect of Punch Size and Baseline Setting on rtPCR Quantification

Because illuminating the sample with light and detecting the fluorescence signal is central to an rtPCR assay, it is expected that the presence of a filter paper punch in the reaction well would have an impact on the detection of the fluorescent signal. To test the influence of punch size on the rtPCR assay, punches of various diameters, 0.5 mm, 1 mm and 2 mm were tested in an rtPCR assay. Individual punches with different diameters were generated from PE-swabs and placed directly into a well of MICROAMP® Optical 96-Well Reaction Plate. Punches were made from negative control PE-swabs; that is, PE-swabs that had not be used to swab a surface. The punches were then subjected to rtPCR analysis.

For the rtPCR analysis, the QUANTIFILER® Duo DNA Quantification reaction kit was utilized. The QUANTIFILER® Duo DNA Quantification kit is designed to simultaneously quantify the total amount of amplifiable human DNA and human male DNA in a sample. The QUANTIFILER® Duo kit contains two primers for amplifying human DNA (Ribonuclease P RNA Component H1) and one TAQMAN® Minor Groove Binder (MGB) probe labeled with the fluorescent dye VIC® for detecting the amplified human target sequence, two primers for amplifying human male DNA (Sex-determining region Y) and TAQMAN® MGB probe labeled with the fluorescent dye FAM™ for detecting the amplified human male target sequence and two primers for amplifying an Internal PCR Control (IPC) template, which is a synthetic nucleotide sequence not found in nature acting as a positive PCR control and TAQMAN® MGB probe labeled with the fluorescent dye NED™ for detecting the amplified IPC DNA. The fluorescent dye ROX™ is included as a passive control.

To analyze the influence of punches and punch size on rtPCR, punches of various sizes were deposited in wells of a MICROAMP® Optical 96-Well Reaction Plate. Wells without punches were also analyzed. To each well were added 10.5 μL QUANTIFILER® Duo Primer Mix, 12.5 μL QUANTIFILER® Duo PCR reaction mix and 2 μL de-ionized water. Also present in the wells was the IPC template control. Quantification reactions were carried out on Applied Biosystems 7500 Real-Time PCR System using the manufacture recommended protocol. The Applied Biosystems 7500 Real-Time PCR System utilizes a CCD detector. The quantification results were analyzed using SDS Software v2.0.6 (Life Technologies). Results from this analysis are shown in FIGS. 3A-3D.

Except for the ROX™ passive reference fluorescent channel, the presence of a filter paper punch in the reaction well results in elevated background florescent signal in the FAM™, VIC® and NED™ fluorescent channels. The magnitude of the background elevation is correlated with the size of the filter paper punch in the reaction well. In addition, it was also observed that the background florescent signal increases after each thermal cycle and the rate increase is apparently correlated with the size of the filter paper punch.

The elevated baseline and the slope of the baseline affect the $C_T$ value determination, which in turn affects the measured DNA quantity. To determine the $C_T$ value, the SDS software first determines the Rn (normalized florescent signal) by dividing the florescent signal in each dye channel by the florescent signal of the passive reference (ROX™) The SDS software then uses the Rn values collected from a predefined range of PCR cycles to serve as baseline. After generating a baseline-subtracted amplification plot of ΔRn versus cycle number, an algorithm defines the cycle number at which the ΔRn value crosses the threshold setting as the threshold cycle ($C_T$).

Figure 4:
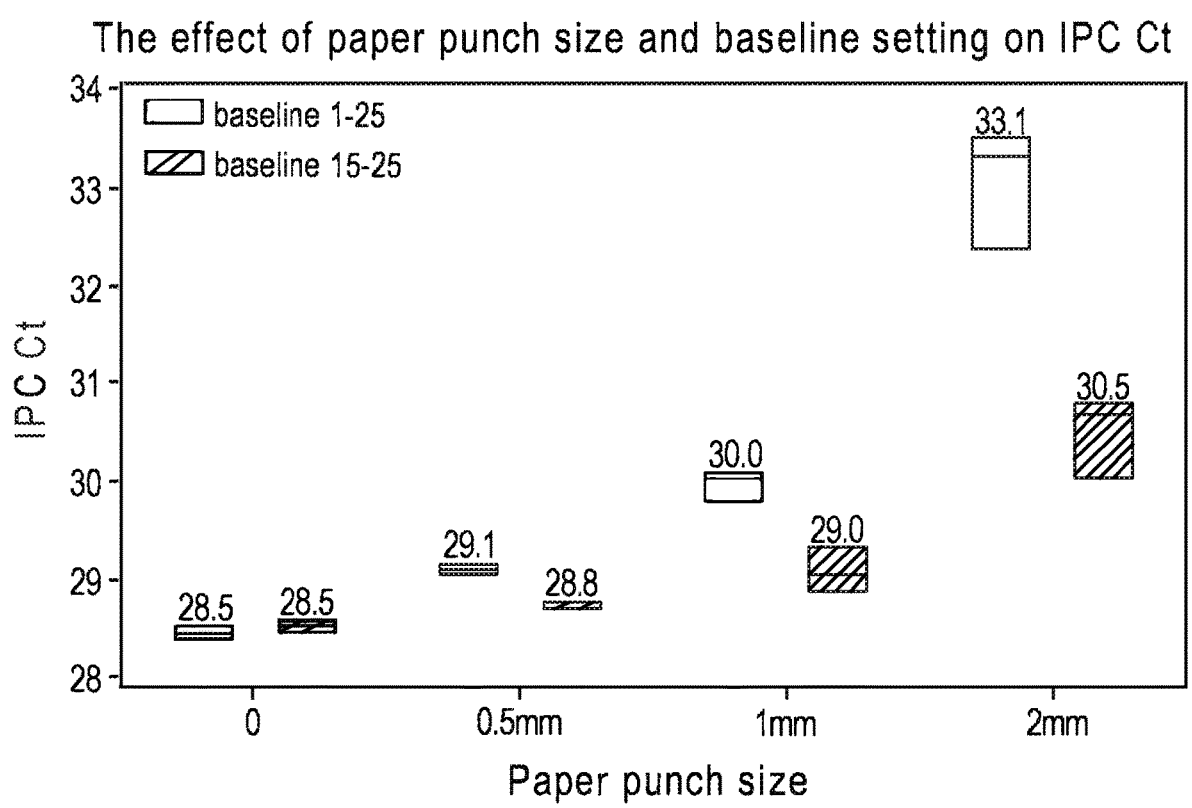
FIG. 4 shows the effect of filter paper punch size and baseline start point/end point setting on Internal PCR Control (IPC) $C_T$ value determination. In this instance, an IPC synthetic DNA sequence was present in the rtPCR reaction mix. Three replicates were tested for each of the reactions containing filter paper with the indicated diameter without added nucleic acid, while four replicate reactions were conducted for the no filter paper control.

The effect of paper punch size and baseline start point/end point setting on the NED™ $C_T$ value is shown in FIG. 4. Amplification of the IPC target is detected based on NED™ fluorescence. Regardless of baseline setting, the presence of a paper punch in the reaction well causes the NED™ $C_T$ value to drift higher. The size of $C_T$ drift is apparently correlated with the size of the paper punch.

Because the presence of a paper punch in a rtPCR reaction causes $C_T$ value to drift higher, and the fact that DNA quantity of the sample is determined based on the $C_T$ value of the sample and those of DNA standards, under estimate of the DNA quantity in the sample will occur when a paper punch is present in the reaction well.

To understand this effect more quantitatively, a 0.5 mm paper punch was placed in a reaction well containing a known amount of a human DNA; human DNA included with the QUANTIFILER® Duo kit as a control. Six reactions were carried out at each DNA input quantity. The optimal baseline setting was set at 15 and 19 for QUANTIFILER® Duo human and male targets and 15 and 25 for IPC target. Measured DNA quantity against the input DNA quantity was shown in Table 1.

TABLE 1

| | STD DNA input (ng) | Duo Human (ng)* | Duo Human STDEV | Duo Male (ng)* | Duo Male STDEV | % diff Human | % diff Male |
|---|---|---|---|---|---|---|---|
| Std 1 | 100.00 | 97.38 | 4.62 | 96.74 | 3.29 | −2.62% | −4.26% |
| Std 2 | 33.40 | 31.19 | 3.16 | 30.73 | 1.96 | −6.61% | −7.98% |
| Std 3 | 11.12 | 11.13 | 0.51 | 10.58 | 0.38 | +0.13% | −4.84% |
| Std 4 | 3.70 | 3.59 | 0.18 | 3.49 | 0.16 | −2.91% | −5.64% |
| Std 5 | 1.24 | 1.15 | 0.03 | 1.10 | 0.06 | −6.87% | −11.41% |
| Std 6 | 0.42 | 0.38 | 0.04 | 0.36 | 0.04 | −10.53% | −13.70% |
| Std 7 | 0.14 | 0.14 | 0.01 | 0.09 | 0.01 | 3.62% | +34.48% |
| Std 8 | 0.05 | 0.06 | 0.01 | 0.04 | 0.01 | +28.55% | −5.99% |

*average of 6 replicates except std 3 and std 6, which are average of 5 replicates When a paper punch was in the reaction well, DNA quantity is under estimated for both human and male targets with DNA input quantity down to 0.42 ng. But the percentage difference is very small. With DNA input down to 0.42 pg, the percentage difference between input quantity and measured quantity is less than 15%. Even with STD 7 and 8, the lower end of the DNA quantity standard range, the percentage difference between input quantity and measured quantity is still less than 34.5%. The DNA quantity over estimation observed at 0.14 ng and 0.05 ng input level is likely due to stochastic effect typical of low copy number samples. This result clearly demonstrated the robustness and accuracy of rtPCR DNA quantification with the presence of a paper punch.

Direct Quantification of Unprocessed Dry Blood Stain on Various Substrates

Dry blood is often found at a crime scene. The applicability of direct qPCR quantification of dry blood deposited on various substrates was tested.

Dry blood stain samples were prepared by pipetting 20 μL blood from a female donor onto five different types of substrates (FIGS. 5A-5E). The liquid blood was spread over the different substrates using a pipette tip and then allowed to dry over 5 days. 40 μL of de-ionized water was applied to each dried blood stain, and the moisten stain was then swabbed with a 20 mm PE-swab. After swabbing, the filter paper stripe was detached from the swab holder and air dried before taking punches. One 0.5 mm paper punch generated from the active sampling area of the 20 mm PE-swab was directly quantified using Quantifier® Duo DNA Quantification assay.

Figure 6:
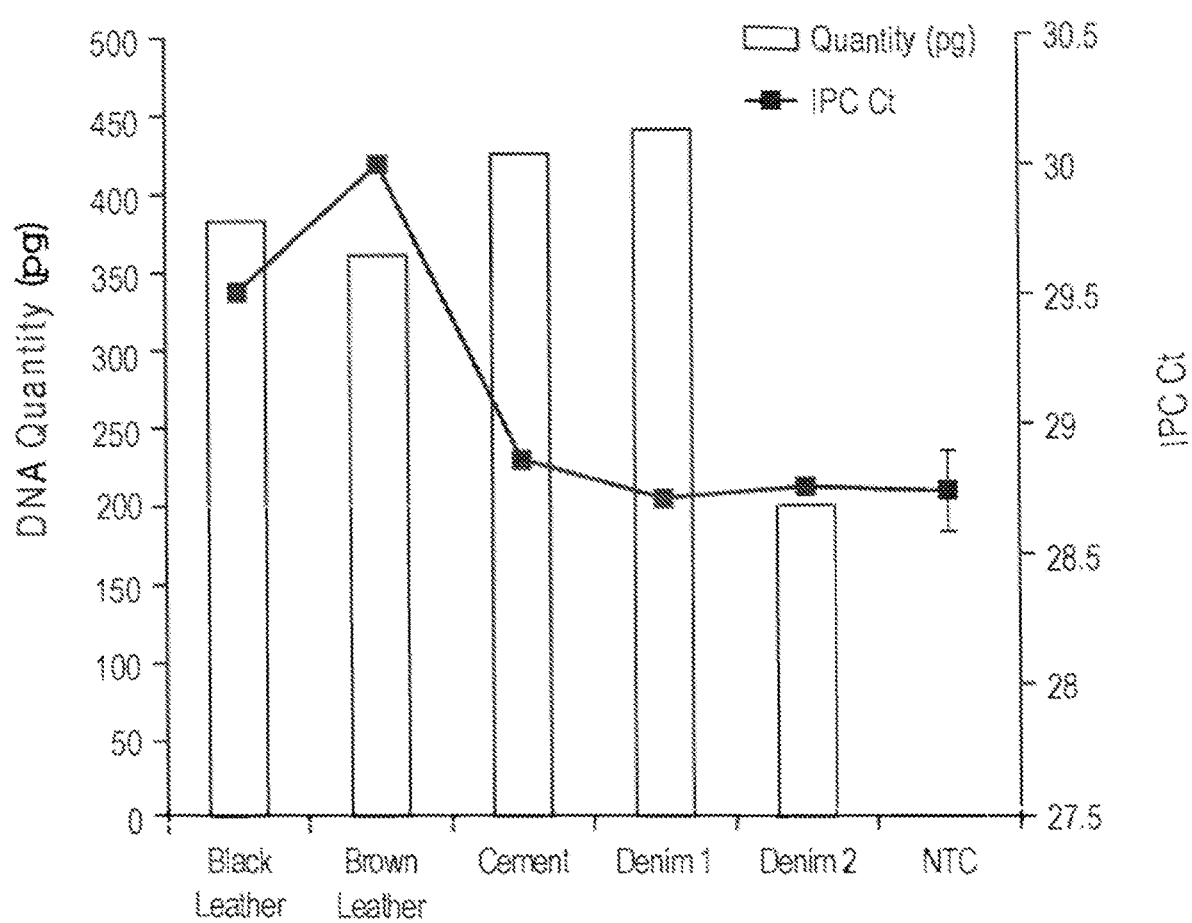
FIG. 6 shows the results of direct rtPCR quantification of unprocessed blood stains collected on a 20 mm PE-swab. A PE-swab was contacted to the indicated substrates and 0.5 mm punches taken from the PE-swab were subjected directly to rtPCR. NTC (no template control).

The measured human DNA quantities and corresponding IPC $C_T$ values were shown in FIG. 6. No male DNA was detected in any of the five samples, which agrees with the fact that the blood is from a female donor. The ability to quickly and accurately identify the gender of a blood stain will help forensic scientists to exclude non-probative samples. Although the blood samples were unprocessed, only the IPC $C_T$ for black leather and brown leather is higher than the average IPC $C_T$ value of two no template control (NTC) reactions. The IPC $C_T$ for cement, denim 1 and denim 2 are less than 0.13 $C_T$ higher than the average IPC $C_T$ values of two NTC reactions.

Direct Quantification of Unprocessed Touch DNA Samples

Figure 7:
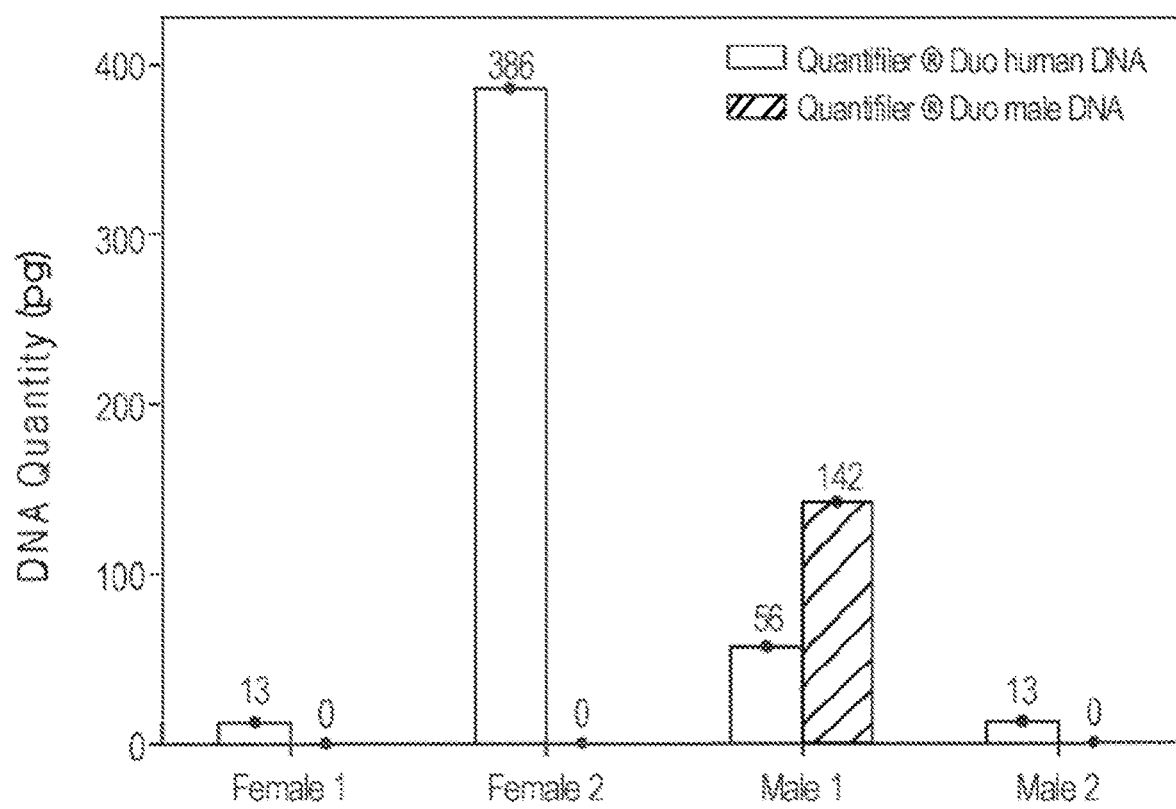
FIG. 7 shows direct rtPCR quantification of unprocessed touch DNA samples. The touch DNA was introduced into the rtPCR in the form of 0.5 mm paper punches generated from the sampling area of a 5 mm PE-swab.

To demonstrate the feasibility of direct quantification of unprocessed touch DNA samples using rtPCR assay, fingerprints from two female and two male donors were collected on transparency films. To increase the amount of DNA on the finger, the donors were asked to touch their face first before pressing their finger on a piece of transparency film. The fingerprint touch samples were stored in a paper envelope to prevent contamination for two weeks before being tested. 104 Ethanol was applied to each fingerprint sample before being swabbed using a 5 mm PE-swab. One 0.5 mm punch generated from the active sampling area of the 5 mm PE-swab from each donor was directly quantified using Quantifier® Duo DNA Quantification kit. The measured human and human male DNA quantities were shown in FIG. 7.

Correct gender call was made in 3 of the 4 samples. No human male DNA was detected in one male sample. The failed detection of male DNA in the one male sample may be due to stochastic effects common to low copy number samples. The other male sample had twice the measured male target relative to the human target DNA. This because the male donor in this instance has a duplicated SRY gene (the male target). This result is the first demonstration of direct quantification of unprocessed touch DNA samples using rtPCR assay.

Direct Quantification Results Can be Used to Determine the DNA Input for STR Analysis That the measured DNA quantity from direct rtPCR assay can be used to determine the optimal DNA input for Short Tandem Repeat (STR) amplification was tested.

A punch or punches generated from a PE-swab contacted to dried blood stains or touch DNA were deposited into a well of a MICROAMP® Optical 96-Well Reaction Plate. 7 μL PCR reaction mix (3.5 μl of GLOBALFILER™ Master Mix and 3.5 μL of IDENTIFILER® direct Primer Mix) was added to each well containing the punches. The thermo-cycling conditions were 95° C./lm, 28, 29 or 30 cycles of (94° C./10 s, 59° C./90 sec), 60° C./10 m and 4 C—hold. After thermal-cycling, 1 μL of the PCR product from each sample was mixed with 9 μL GENESCAN®500 size standard and deionized formamide and analyzed using a ABI 3130xl capillary electrophoresis instrument using the following conditions: Oven: 60° C., Pre-run: 15 kV, 180 s, Injection: 3 kV, 10 s, Run: 15 kV, 1500 s, Capillary length: 36 cm, Separation polymer: POP4™ polymer and dye set: G5. The resulting STR electropherograms were analyzed using GENEMAPPER® ID-X software (Applied Biosystems).

Swabs of Dried Blood

Figure 8:
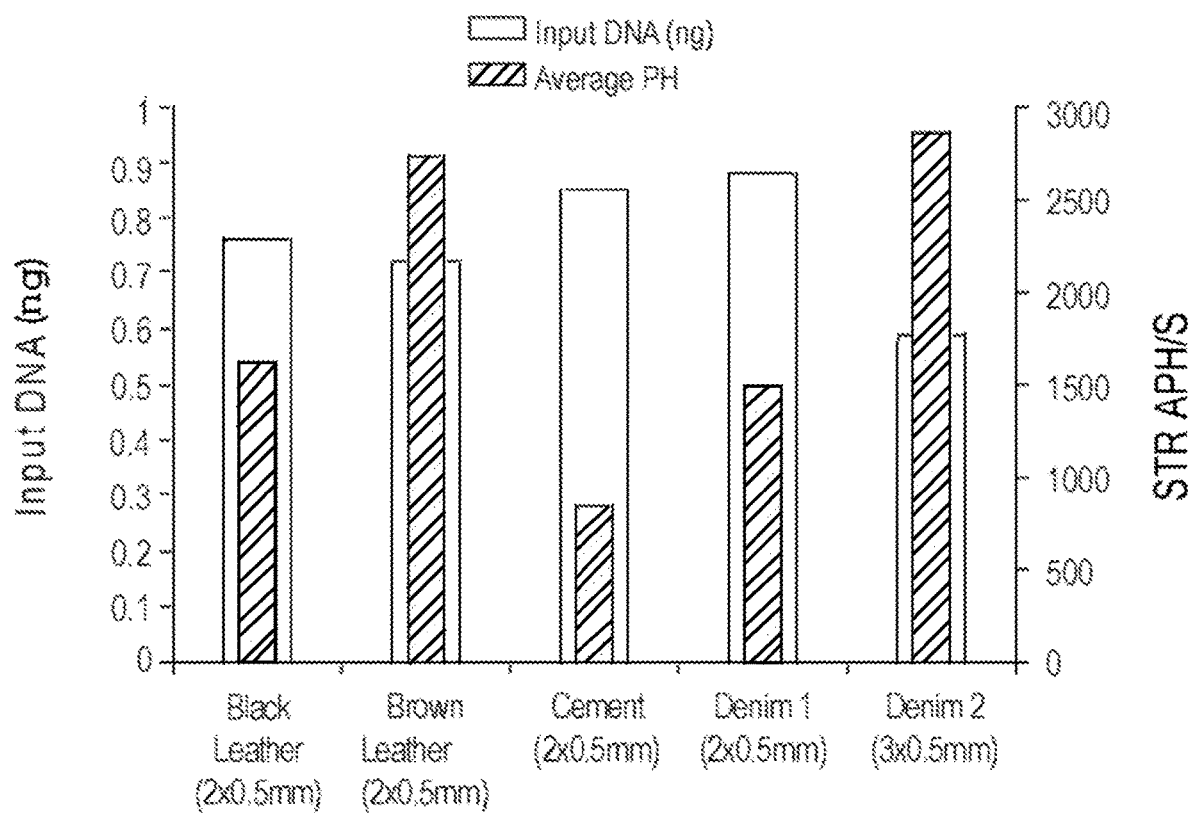
FIG. 8 shows the correlation between input DNA amount, as determined by direct quantification, and corresponding average peak height of the STR profile obtained from the direct amplification of punches taken from the same PE-swab. 28 PCR cycles were used.
Figure 9:
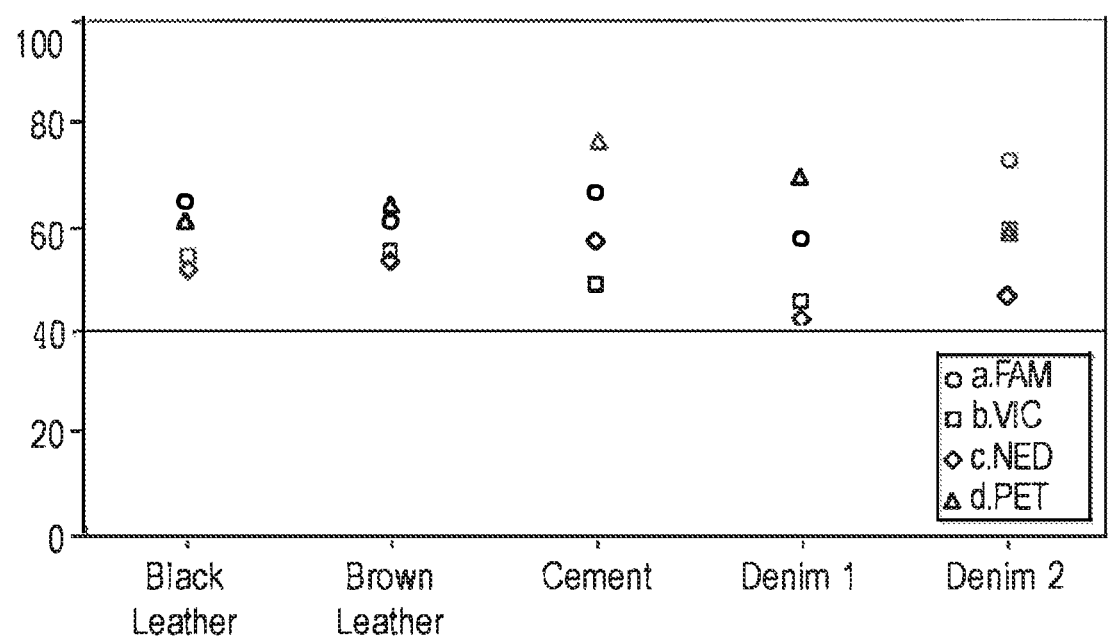
FIG. 9 shows the intra-color balance of STR profiles obtained based on using DNA amounts determined by direct quantification from dry blood stain samples from the various indicated substrates.
Figure 10A:
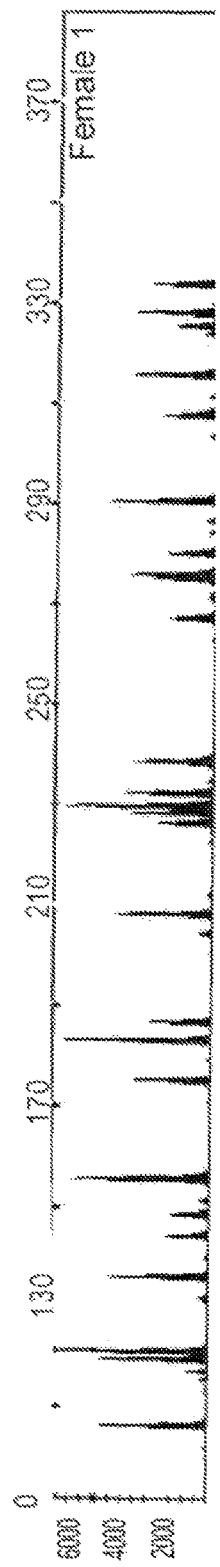
FIGS. 10A-10D show the results of a STR profiles obtained from touch DNA samples, wherein the amount of input DNA used for the STR assay was determined by direct quantification from PE-swab punches.
Figure 10B:
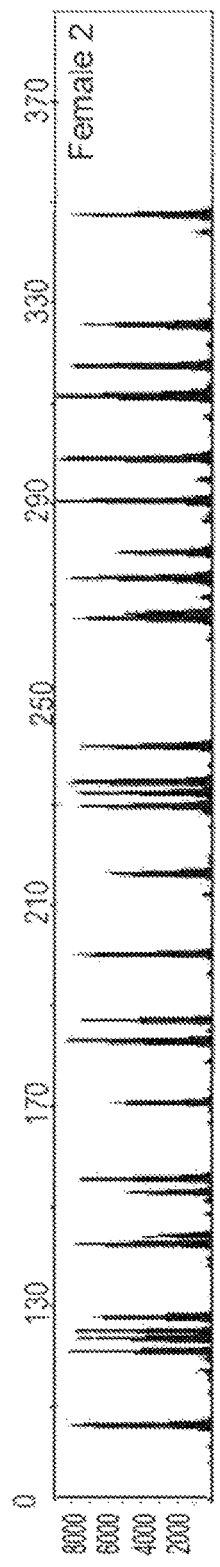
Figure 10C:
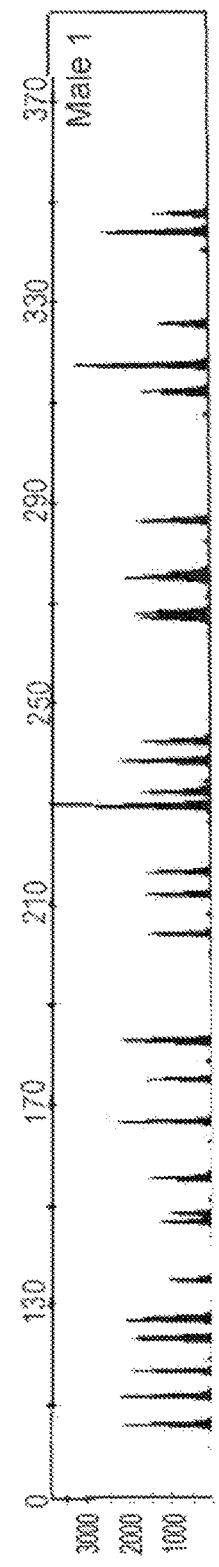
Figure 10D:
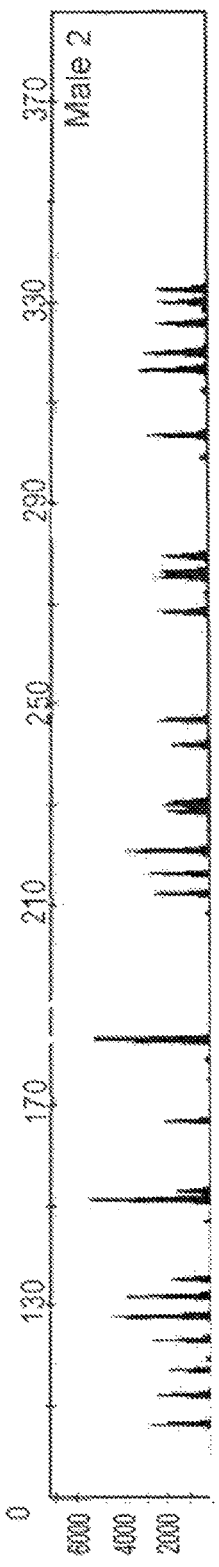

Full STR profiles with high profile quality were obtained from all five dry blood stain samples. FIG. 8 shows the correlation between DNA input amount and average peak height of the STR profiles. The intra-color balance for all four dye channels and for all five samples are above 40% (FIG. 9). These results demonstrated for the first time that dry blood stains of forensic casework sample types can be directly quantified and the quantification results can be used to estimate the optimal DNA input for direct STR amplification. The ability to obtain both DNA quantity and gender information from unprocessed blood stains will greatly increase the capability of the crime labs for processing such samples.

Swabs from Touch Samples

The recommended DNA input quantity for GLOBAL-FILER™ kit for casework is 1 ng of DNA in a 254 PCR reaction. Based on the direct quantification results determined for the touch DNA samples described above, and shown in FIG. 7, a single punch from female 1 and from male 2 are each estimated to possess of about 13 pg. Based on this four 1 mm punches (208 pg of DNA) were used in the STR amplification reaction. For female 2 and male 1, one 0.5 mm punch was used in STR PCR, which is 386 pg and 56 pg respectively. The PCR reactions were carried out for 30 cycles.

Figure 11:
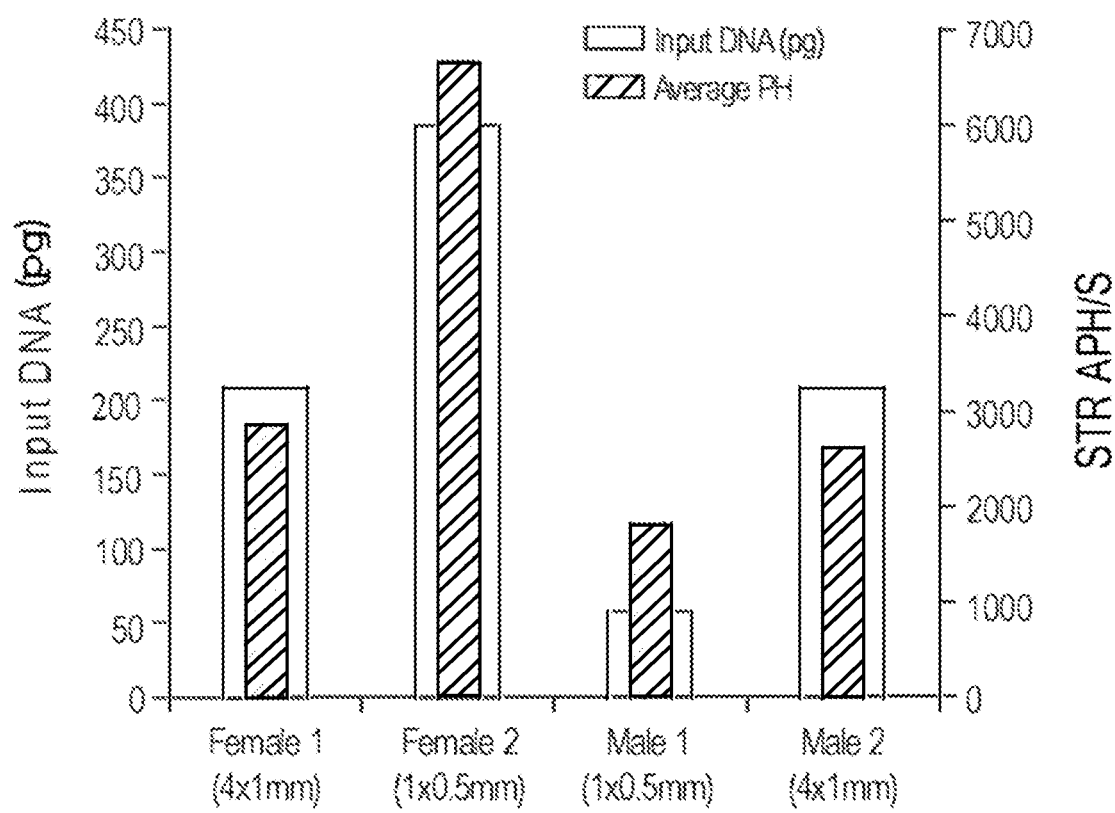
FIG. 11 shows the correlation between DNA input, based on direct quantification, and corresponding average peak height of the STR profile obtained from direct STR amplification from punches from the same PE-swab. 30 PCR cycles were used.

Full STR profiles were obtained for all four touch DNA samples (FIGS. 10A-10D). PCR input DNA quantity is also correlated well with the average peak height of the STR results (FIG. 11). Off scale peaks were observed with the profile in female 2, which is in agreement with the amount of input DNA and the fact that PCR was run an additional cycle.

Because of the small size of the punches, smaller PCR reaction volume can be used to increase STR sensitivity. Instead of the standard 25 µL, 7 µL PCR reaction volume was used in this study and it can accommodate four 1 mm paper punches.

The invention claimed is:

1. A method for quantifying DNA from a sample, the method comprising:
    contacting one or more objects with a paper to collect nucleic acid;
    depositing the paper into a vessel;
    performing a real-time polymerase chain reaction (rtPCR) within the vessel and detecting the level of fluorescence emitted from the vessel during rtPCR; and
    determining the quantity of nucleic acid on the one or more objects by correlating the level of fluorescence to the quantity of nucleic acid on the one or more objects.

2. The method of claim 1, wherein one or more objects possess a fingerprint.

3. The method of claim 1, wherein the annealing and extension temperatures used in the rtPCR are the same.

4. The method of claim 1, wherein the rtPCR is multiplex rtPCR.

5. The method of claim 1, wherein the fluorescent detection comprises use of a fluorescent reporter probe.

6. The method of claim 5, wherein the fluorescent reporter probe is coupled with a quencher.

7. The method of claim 1, wherein the area of the paper is equal to or less than the area of a circle with a diameter of 3 mm.

8. The method of claim 1, wherein the area of the paper is equal to or less than the area of a circle with a diameter of 2 mm.

9. The method of claim 1, wherein the area of the paper is equal to or less than the area of a circle with a diameter of 1 mm.

10. The method of claim 5, wherein the one or more fluorescent reporter probes comprise a non-specific double strand intercalating dye, 5'-exonuclease probe, molecular beacon, hybridization probe, primer with attached probe tail sequence in a stem-loop structure, or combination thereof.

11. The method of claim 1, wherein the level of fluorescence emitted from the vessel during rtPCR is detected by a charge-coupled device while the paper is in the vessel.

12. The method of claim 1, wherein the paper is not subjected to nucleic acid extraction prior to depositing into the vessel and performing rtPCR within the vessel.

13. The method of claim 1, further comprising determining an amount of input DNA for short tandem repeat (STR) analysis based on the determined quantity of nucleic acid on the one or more objects.

14. The method of claim 12, further comprising performing a direct STR amplification.

15. The method of claim 1, wherein the nucleic acid on the one or more objects is from blood, dry blood, whole blood, plasma, serum, saliva, sweat, vaginal secretions, semen, tissues, urine, cerebrospinal fluid, or is a touch nucleic acid.

16. The method of claim 1, wherein the paper contains fibers selected from cellulosic fibers, fibers from Esparto grass, bagasse, kemp, flax, lignaceous fibers, rayon, polyethylene, polypropylene, fibers containing hydroxyl groups, and mixtures of any of the foregoing fibers.

17. The method of claim 1, wherein the paper is a filter paper.

18. The method of claim 17, wherein one or more of a weak base, a chelating agent, a detergent and combinations thereof are sorbed to the filter paper before depositing the filter paper into the vessel.

19. The method of claim 1, further comprising performing the rtPCR in the presence of an internal PCR control synthetic DNA sequence.

20. A method for quantifying DNA from a sample, the method comprising:
    contacting one or more objects with a paper to collect nucleic acid;
    depositing the paper into a vessel;
    without subjecting the paper to nucleic acid extraction, performing a real-time polymerase chain reaction (rtPCR) within the vessel and detecting the level of fluorescence emitted from the vessel during rtPCR;
    determining the quantity of nucleic acid on the one or more objects by correlating the level of fluorescence to the quantity of nucleic acid on the one or more objects;
    determining an amount of input DNA for short tandem repeat (STR) analysis based on the determined quantity of nucleic acid on the one or more objects; and
    optionally performing a direct STR amplification.

* * * * *

UNITED STATES PATENT AND TRADEMARK OFFICE
CERTIFICATE OF CORRECTION

PATENT NO. : 11,643,680 B2
APPLICATION NO. : 17/209957
DATED : May 9, 2023
INVENTOR(S) : Jason Yingjie Liu Page 1 of 1

It is certified that error appears in the above-identified patent and that said Letters Patent is hereby corrected as shown below:

On the Title Page

In Column 1, under Related U.S. Application Data, delete "(60)" and insert --(62)--, therefor.

Signed and Sealed this
Sixteenth Day of July, 2024

*Katherine Kelly Vidal*
Katherine Kelly Vidal
*Director of the United States Patent and Trademark Office*